United States Patent
Kumano et al.

(10) Patent No.: US 10,908,170 B2
(45) Date of Patent: Feb. 2, 2021

(54) METHOD FOR MEASURING CLOTTING TIME, MEASUREMENT DEVICE FOR CLOTTING TIME, AND REAGENT KIT

(71) Applicants: SYSMEX CORPORATION, Kobe (JP); SCHOOL JURIDICAL PERSON HIGASHI-NIPPON-GAKUEN, Hokkaido (JP)

(72) Inventors: Osamu Kumano, Kobe (JP); Haruki Yamaguchi, Kobe (JP); Takeshi Suzuki, Kobe (JP); Masahiro Ieko, Ishikari-gun (JP)

(73) Assignees: SYSMEX CORPORATION, Kobe (JP); SCHOOL JURIDICAL PERSON HIGASHI-NIPPON-GAKUEN, Hokkaido (JP)

(*) Notice: Subject to any disclaimer, the term of this patent is extended or adjusted under 35 U.S.C. 154(b) by 18 days.

(21) Appl. No.: 15/219,846

(22) Filed: Jul. 26, 2016

(65) Prior Publication Data
US 2018/0031582 A1    Feb. 1, 2018
US 2018/0348237 A9   Dec. 6, 2018

(30) Foreign Application Priority Data
Jul. 30, 2015 (JP) .................................. 2015-150815

(51) Int. Cl.
*G01N 33/86* (2006.01)

(52) U.S. Cl.
CPC ......... *G01N 33/86* (2013.01); *G01N 2400/40* (2013.01)

(58) Field of Classification Search
None
See application file for complete search history.

(56) References Cited

U.S. PATENT DOCUMENTS

| | | | |
|---|---|---|---|
| 5,451,509 A * | 9/1995 | Speck | A61K 33/24 435/13 |
| 5,705,396 A | 1/1998 | Fickenscher et al. | |
| 6,284,871 B1 * | 9/2001 | Mertens | C07K 14/755 530/383 |
| 2003/0199014 A1 | 10/2003 | Rosen et al. | |
| 2008/0241941 A1 * | 10/2008 | Okuda | A01K 67/0337 436/69 |
| 2008/0260858 A1 * | 10/2008 | Morrissey | A61K 38/36 424/638 |
| 2011/0014640 A1 | 1/2011 | Yamamoto et al. | |
| 2015/0366814 A1 * | 12/2015 | Hu | A61K 9/4825 514/560 |

FOREIGN PATENT DOCUMENTS

| | | |
|---|---|---|
| CN | 101226201 A | 7/2008 |
| CN | 101983338 A | 3/2011 |
| EP | 1975622 A1 | 10/2008 |
| EP | 2423687 A2 | 2/2012 |
| EP | 2790024 A1 | 10/2014 |
| JP | 2001255332 A | 9/2001 |
| JP | 2009-244027 A | 10/2009 |
| WO | 2006088741 A2 | 8/2006 |

OTHER PUBLICATIONS

Communication dated Oct. 27, 2016 issued for the corresponding European application No. 16181820.8.
Communication dated Jan. 29, 2019, from the Japanese Patent Office in corresponding JP application No. 2015-150815.

* cited by examiner

*Primary Examiner* — Scott Long
*Assistant Examiner* — Evelyn Y Pyla
(74) *Attorney, Agent, or Firm* — Sughrue Mion, PLLC

(57) ABSTRACT

Disclosed is a method for measuring a clotting time, including the steps of:

(A) mixing a blood sample, an activator, a phospholipid, and a nickel ion-forming compound to obtain a specimen; and (B) mixing the specimen obtained in step (A) with a calcium salt to prepare a measurement specimen and measuring the clotting time of the measurement specimen.

12 Claims, 8 Drawing Sheets

METHOD FOR MEASURING CLOTTING TIME, MEASUREMENT DEVICE FOR CLOTTING TIME, AND REAGENT KIT

CROSS REFERENCE TO RELATED APPLICATIONS

This application claims priority from prior Japanese Patent Application No. 2015-150815, filed on Jul. 30, 2015, entitled "METHOD FOR MEASURING CLOTTING TIME, MEASUREMENT DEVICE FOR CLOTTING TIME, CLOTTING TIME MEASURING REAGENT, AND REAGENT KIT", the entire contents of which are incorporated herein by reference.

TECHNICAL FIELD

The present invention relates to a method for measuring a clotting time, a measurement device for a clotting time, a clotting time measuring reagent, and a reagent kit.

BACKGROUND

Activated partial thromboplastin time (APTT) is used to monitor the concentration of heparin as an anticoagulant (U.S. Pat. No. 5,705,396). U.S. Pat. No. 5,705,396 describes that, with use of an APTT measuring reagent containing a copper or zinc salt, the activity of heparin is decreased when the APTT is measured.

However, there is a need to measure the clotting time at high sensitivity even if a heparin-containing sample is used.

SUMMARY OF THE INVENTION

The scope of the present invention is defined solely by the appended claims, and is not affected to any degree by the statements within this summary.

A first aspect of the present invention includes a method for measuring a clotting time, including the steps of:

(A) mixing a blood sample, an activator, a phospholipid, and a nickel ion-forming compound to obtain a specimen; and (B) mixing the specimen obtained in step (A) with a calcium salt to prepare a measurement specimen and measuring the clotting time of the measurement specimen.

A second aspect of the present invention includes a measurement device for a clotting time, including: a specimen preparing section that mixes a blood sample, an activator, a phospholipid, a nickel ion-forming compound, and a calcium salt to prepare a measurement specimen; a detection unit that obtains clotting information showing a change associated with a clotting reaction from the measurement specimen obtained in the specimen preparing section; a calculator that calculates the clotting time of the measurement specimen based on the optical information obtained by the detection unit; and a reagent accommodating portion that accommodates an activator, a phospholipid, a nickel ion-forming compound, and a calcium salt; wherein the specimen preparing section obtains the activator, the phospholipid, and the nickel ion-forming compound from the reagent accommodating portion, the activator, and mixes the activator, the phospholipid, the nickel ion-forming compound, and the blood sample to prepare a specimen, and the specimen preparing section obtains the calcium salt from the reagent accommodating portion, and mixes the calcium salt with the specimen to obtain a measurement specimen.

A third aspect of the present invention includes a clotting time measuring reagent that is used in the method for measuring a clotting time, which contains a nickel ion-forming compound.

A fourth aspect of the present invention includes a reagent kit including a first reagent containing an activator and a phospholipid accommodated in a first reagent container, a second reagent containing a nickel ion-forming compound accommodated in a second reagent container, and a third reagent containing a calcium salt accommodated in a third reagent container.

DETAILED DESCRIPTION OF THE PREFERRED EMBODIMENTS

1. Method for Measuring Clotting Time

Figure 1:
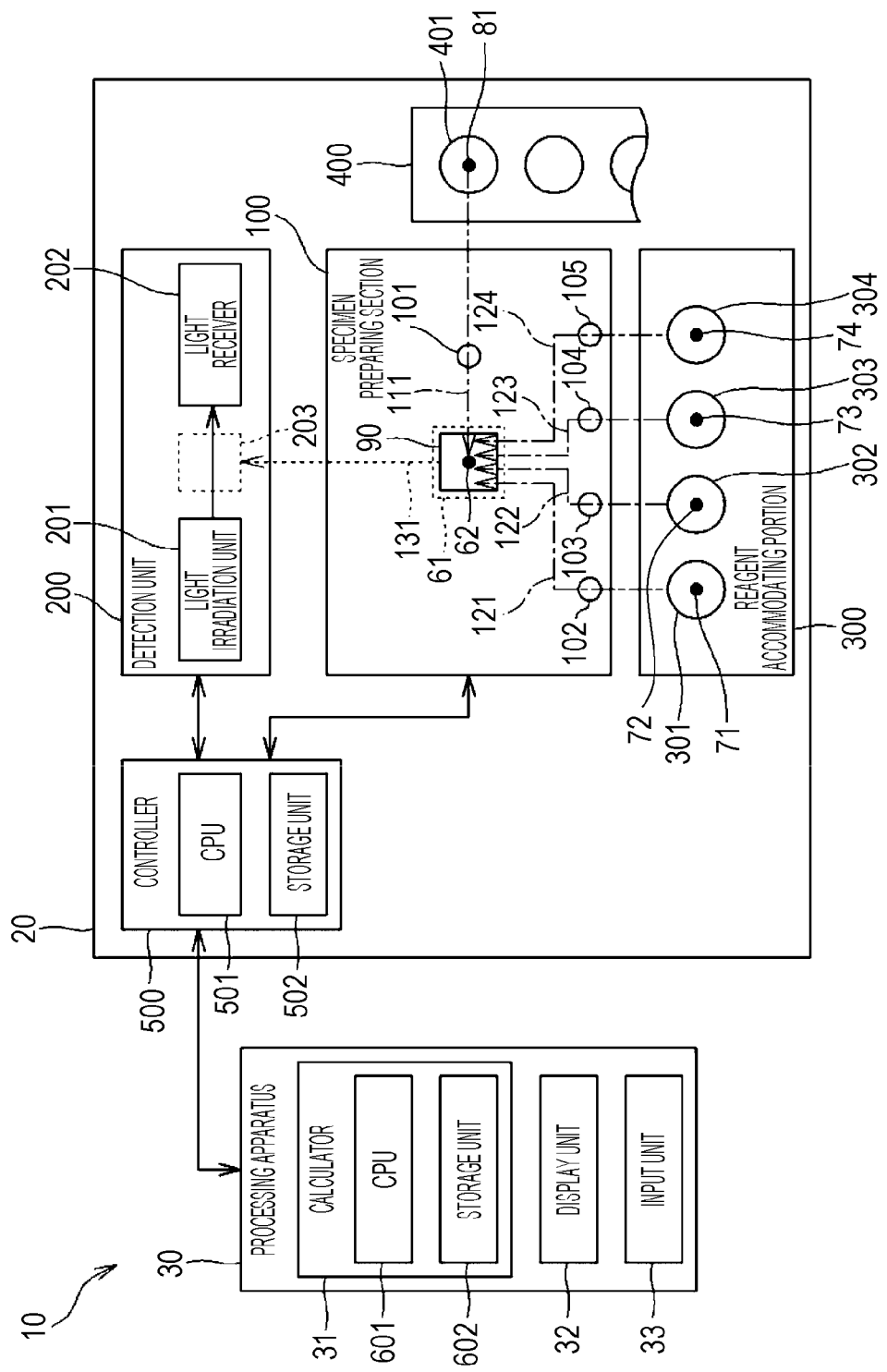
FIG. 1 is a configuration diagram of a measurement device for a clotting time.

The method for measuring a clotting time according to an embodiment (hereinafter simply referred to as "measurement method") includes the steps of: (A) mixing a blood sample, an activator, a phospholipid, and a nickel ion-forming compound to obtain a specimen; and (B) mixing the specimen obtained in step (A) with a calcium salt to prepare a measurement specimen and measuring the clotting time of the measurement specimen. In the measurement method according to the embodiment, a blood sample, an activator, a phospholipid, and a nickel ion-forming compound are mixed in obtaining a specimen in step (A). Therefore, the measurement method according to the embodiment allows the clotting time to be measured at high sensitivity even if a heparin-containing sample is used.

The term "specimen" used herein means a mixture of a blood sample, an activator, a phospholipid, and a nickel ion-forming compound. The term "measurement specimen" means a mixture of a blood sample, an activator, a phospholipid, a nickel ion-forming compound, and a calcium salt.

Examples of the blood sample include plasma, but are not particularly limited thereto. The term "normal plasma" used herein means plasma obtained from blood of a healthy individual. The normal plasma may be commercially available normal plasma. Examples of test plasma include plasma obtained from a subject, and plasma obtained from a subject and contains heparin, but are not particularly limited.

The activator should be a substance having an effect of activating contact factors involved in the intrinsic coagulation pathway. Examples of the contact factors include prekallikrein, high-molecular-weight kininogen, and factors XII and XI, but are not particularly limited thereto. Examples of the activator include ellagic acid compounds, silica, kaolin, and diatomaceous earth (e.g. product name: Celite (registered trademark), manufactured by Celite Corporation), but are not particularly limited thereto. These activators may be used singly, or as a mixture of two or more kinds thereof. The term "ellagic acid compound" means a concept including ellagic acid, and a salt and a metal complex of ellagic acid.

A phospholipid accelerates a blood clotting reaction. The phospholipid is a lipid having a phosphoric ester site in a molecular structure. The phospholipid may be a naturally occurring or synthetic phospholipid. Examples of the naturally occurring phospholipid include phospholipids derived from animals such as rabbit, bovine, porcine, chicken, and human; and phospholipids derived from plants such as soybean, but are not limited thereto. Examples of the phospholipids derived from animals include phospholipids derived from rabbit brain, bovine brain, yolk, human placenta, and the like, but are not limited thereto. Specific examples of the phospholipid include glycerophospholipids such as phosphatidylethanolamine, phosphatidylcholine, and phosphatidylserine, but are not limited thereto. Among these phospholipids, phosphatidylethanolamine, phosphatidylcholine, and phosphatidylserine are preferred from the viewpoint of efficient progression of the blood clotting reaction. These phospholipids may be used singly, or as a mixture of two or more kinds thereof. Examples of the fatty acid side chains in phospholipids include palmitoyl, oleoyl, and stearoyl groups, but are not particularly limited thereto. These fatty acid side chains may be appropriately selected as long as the blood clotting reaction is not hindered.

The nickel ion-forming compound should be a compound that forms nickel ions in a blood sample. The nickel ion-forming compound is preferably a compound that forms divalent cations. Examples of the nickel ion-forming compound include nickel acetate, nickel phosphide, nickel sulfide, nickel chloride, and nickel sulfate, but are not particularly limited thereto. Among these nickel ion-forming compounds, nickel acetate is preferred. These nickel ion-forming compounds may be used singly, or as a mixture of two or more kinds thereof.

The calcium salt should be a salt that forms calcium ions in a measurement specimen. Examples of the calcium salt include calcium chloride, calcium sulfate, calcium nitrite, calcium carbonate, calcium lactate, and calcium tartrate, but are not particularly limited thereto. These calcium salts may be used singly, or as a mixture of two or more kinds thereof.

In step (A), a blood sample, an activator, a phospholipid, and a nickel ion-forming compound are mixed to obtain a specimen. Prior to step (A), the blood sample may be heated to a temperature appropriate for performing the clotting reaction. Usually, the heating temperature of the blood sample is preferably from 30 to 45° C. and more preferably from 36 to 38° C.

In step (A), the order of mixing the blood sample, activator, phospholipid, and nickel ion-forming compound is not particularly limited. Step (A) is divided into, for example, the following aspects:

(Aspect 1)

mixing a blood sample, an activator, and a phospholipid to obtain a mixture, and adding a nickel ion-forming compound thereto;

(Aspect 2)

mixing a blood sample with a nickel ion-forming compound, and adding an activator and a phospholipid thereto; and (Aspect 3)

simultaneously adding an activator, a phospholipid, and a nickel ion-forming compound to a blood sample.

In Aspect 1, step (A) includes, for example, the following step (A1-1) and step (A1-2):

(A1-1) mixing a blood sample, an activator, and phospholipid to obtain a mixture; and (A1-2) mixing the mixture obtained in step (A1-1) with a nickel ion-forming compound.

Hereinafter, the measurement method according to the embodiment will be described with reference to Aspect 1, but is not particularly limited thereto. In step (A1-1), a blood sample, an activator, and a phospholipid are mixed to obtain a mixture. The order of mixing the blood sample, activator, and phospholipid is not particularly limited. The activator and phospholipid may be mixed simultaneously with the blood sample. The activator and phospholipid may be mixed with the blood sample at different times. In this case, the phospholipid may be added after the activator is added to the blood sample, or alternatively, the activator may be added after the phospholipid is added to the blood sample.

In step (A1-1), the amount of the activator to be mixed with the blood sample should be an amount at which the concentration of the activator in the measurement specimen is a predetermined concentration. The concentration of the activator in the measurement specimen may be appropriately set depending on the type of activator. When the activator is an ellagic acid compound, usually, the concentration of the activator in the measurement specimen is preferably from 3.5 to 150 µM and more preferably from 10 to 50 µM. When the activator is silica, usually, the concentration of the activator in the measurement specimen is preferably from 0.04 to 0.4 mg/mL and more preferably from 0.07 to 0.2 mg/mL.

In step (A1-1), the amount of the phospholipid to be mixed with the blood sample should be an amount at which the concentration of the phospholipid in the measurement specimen is a predetermined concentration. The concentration of the phospholipid in the measurement specimen may be appropriately set depending on the type of phospholipid. When the phospholipid is phosphatidylethanolamine, usually, the concentration of the phospholipid in the measurement specimen is preferably from 1 to 150 µg/mL and more preferably from 5 to 50 µg/mL. When the phospholipid is phosphatidylcholine, usually, the concentration of the phospholipid in the measurement specimen is preferably from 1 to 100 µg/mL and more preferably from 5 to 80 µg/mL. When the phospholipid is phosphatidylserine, usually, the concentration of the phospholipid in the measurement specimen is preferably from 0.1 to 50 µg/mL and more preferably from 1 to 10 µg/mL. When the phospholipid is a mixture of two or more kinds of phospholipids, usually, the concentration of each of the phospholipids in the measurement specimen is preferably from 5 to 400 µg/mL and more preferably from 20 to 100 µg/mL.

The heating temperature when mixing the blood sample, the activator and/or the phospholipid should be a temperature appropriate for performing the blood clotting reaction. Usually, the heating temperature is preferably from 30 to 45° C. and more preferably from 36 to 38° C. Usually, the heating time is preferably from 10 to 150 seconds and more preferably from 30 to 90 seconds.

In step (A1-2), the mixture obtained in step (A1-1) is mixed with a nickel ion-forming compound to obtain a specimen.

In step (A1-2), the amount of the nickel ion-forming compound to be mixed with the mixture obtained in step (A1-1) should be an amount at which the nickel ion-forming compound in the measurement specimen has a predetermined final concentration. The final concentration of the nickel ion-forming compound in the measurement specimen is preferably 0.1 µM or more, more preferably 0.1 mM or more, and preferably less than 10 mM, more preferably 5 mM or less.

The heating temperature when mixing the mixture obtained in step (A1-1) with the nickel ion-forming compound should be a temperature appropriate for performing the blood clotting reaction. Usually, the temperature is preferably from 30 to 45° C. and more preferably from 36 to 38° C. Usually, the heating time is preferably from 30 to 420 seconds and more preferably from 100 to 350 seconds.

From the viewpoint of effectively preventing the clotting time from becoming too long during the measurement of clotting time, the mixture obtained in step (A1-1) is preferably mixed with a nickel ion-forming compound in step (A1-2) within 150 seconds, preferably within 60 seconds after the end of mixing the blood sample, activator, and phospholipid in step (A1-1).

In step (B), the specimen obtained in step (A) is mixed with a calcium salt to prepare a measurement specimen, and the clotting time of the measurement specimen is measured.

The amount of the calcium salt to be mixed with the specimen may be an amount at which the concentration of the calcium salt in the measurement specimen is a predetermined concentration. The concentration of calcium salt in the measurement specimen is preferably from 2 to 20 mM and more preferably from 4 to 10 mM.

In step (B), the specimen may be heated to an appropriate temperature to carry out a clotting reaction before adding the calcium salt to the specimen. The heating temperature of the specimen is preferably 30° C. or more and more preferably 36° C. or more from the viewpoint of reactivity in the clotting reaction. The heating temperature of the specimen is preferably 45° C. or less and more preferably 38° C. or less from the viewpoint of protein stability. In this case, the heating time is preferably 1 minute or more and more preferably 2 minutes or more from the viewpoint of reactivity in the clotting reaction. The heating time is preferably 6 minutes or less and more preferably 5 minutes or less from the viewpoint of protein stability.

The clotting time of the measurement specimen can be examined based on clotting information. Examples of the clotting information include changes in the transmitted or scattered light when the measurement specimen is irradiated with light and changes in the viscosity of the measurement specimen, but are not particularly limited thereto. In this case, the clotting time of the measurement specimen can be examined by emitting light to the measurement specimen, and monitoring changes in the transmitted light passed through the measurement specimen or the scattered light from the measurement specimen, or monitoring changes in the viscosity of the measurement specimen. The term "clotting time" used herein means an activated partial thromboplastin time. The clotting time is a time from when the addition of the calcium salt to the specimen starts till when the plasma clots.

The clotting of plasma can be determined using as an indicator, for example, the fact that the light from the measurement specimen irradiated with light does not change any more, or the fact that the viscosity of the measurement specimen does not change any more.

2. Measurement Device for Clotting Time

[Overall Configuration of Measurement Device]

An example of the measurement device for a clotting time (hereinafter, simply referred to as "measurement device") to be used for the measurement method as described above will be described with reference to the attached drawings. As shown in FIG. 1, a measurement device 10 includes a measurement unit 20 and a processing apparatus 30. The measurement unit 20 and the processing apparatus 30 are communicably connected to each other.

[Configuration of Measurement Unit]

As shown in FIG. 1, the measurement unit 20 includes a specimen preparing section 100, a detection unit 200, and a reagent accommodating portion 300, a sample accommodating portion 400 accommodating a blood sample, and a controller 500.

The specimen preparing section 100 obtains a reagent from the reagent accommodating portion 300 and also obtains a blood sample from the sample accommodating portion 400. The specimen preparing section 100 mixes the obtained reagent with the obtained blood sample based on a predetermined procedure to prepare a measurement specimen. The specimen preparing section 100 includes a sample transporting section 111, a first reagent transporting section 112, a second reagent transporting section 113, a third reagent transporting section 114, a fourth reagent transporting section 115, and a cuvette transporting section 131. The sample transporting section 111 has a first nozzle 101. The sample transporting section 111 obtains the blood sample accommodated in the sample accommodating portion 400. The sample transporting section 111 discharges the obtained blood sample into a cuvette 90. The first reagent transporting section 112 has a second nozzle 102. The first reagent transporting section 112 obtains a reagent accommodated in a first container 301 of the reagent accommodating portion 300 through the second nozzle 102. The first reagent transporting section 112 discharges the obtained reagent into the cuvette 90. The second reagent transporting section 113 has a third nozzle 103. The second reagent transporting section 113 obtains a reagent accommodated in a second container 302 of the reagent accommodating portion 300 through the third nozzle 103. The second reagent transporting section 113 discharges the obtained reagent into the cuvette 90. The third reagent transporting section 114 obtains a reagent accommodated in a third container 303 of the reagent accommodating portion 300 through a fourth nozzle 104. The third reagent transporting section 114 discharges the obtained reagent into the cuvette 90. The fourth reagent transporting section 115 obtains a reagent accommodated in a fourth container 304 of the reagent accommodating portion 300 through a fifth nozzle 105. The fourth reagent transporting section 115 discharges the obtained reagent into the cuvette 90. The cuvette transporting section 131 transports the cuvette 90 accommodating a prepared measurement specimen to the detection unit 200.

The detection unit 200 includes a light irradiation unit 201, a light receiver 202, and a second cuvette mounting portion 203. The light irradiation unit 201 has a light source of light emitted to a measurement specimen. The wavelength of emitted light should be a wavelength suitable for monitoring the change with the progress of the clotting reaction of blood. The light receiver 202 receives light from the measurement specimen. The light from the measurement specimen may be transmitted or scattered light. The light receiver 202 outputs an electric signal corresponding to the amount of the received light to a calculator 31 of the processing apparatus. The second cuvette mounting portion 203 is provided between the light irradiation unit 201 and the light receiver 202. The cuvette 90 transported from the specimen preparing section 100 is placed in the second cuvette mounting portion 203.

The reagent accommodating portion 300 accommodates a reagent used for measurement of clotting time. In the embodiment, the reagent accommodating portion 300 includes a first container 301 that accommodates an activator, a second container 302 that accommodates a phospholipid, a third container 303 that accommodates a nickel ion-forming compound, and a fourth container 304 that accommodates a calcium salt. An identifier for identifying the kind of reagent accommodated in the container is provided in each of the first to fourth containers. Examples of the identifiers include bar codes, but are not particularly limited thereto. In the embodiment, the first container 301 and the second container 302 as different containers are provided in the reagent accommodating portion 300. However, since the activator and phospholipid may be simultaneously mixed with a blood sample, the activator and phospholipid may be accommodated in one common container in place of the first and second containers. In this case, the first reagent transporting section 112 and the second reagent transporting section 113 are one common transporting section.

The sample accommodating portion 400 accommodates a blood sample. In the embodiment, the sample accommodating portion 400 includes a plurality of sample containers 401. The sample accommodating portion 400 transports the sample containers 401 accommodating desired blood samples to a predetermined sample aspirating position. Identifiers for identifying the kinds of blood samples accommodated in the containers are provided in the sample containers 401. Examples of the identifiers include bar codes, but are not particularly limited thereto.

The controller 500 includes a central processing unit (CPU) 501 and a storage unit 502. The controller 500 is composed of a computer. The CPU 501 executes the computer program stored in the storage unit 502. Thus, the CPU 501 prepares the specimen in the specimen preparing section 100 and provides optical information on a measurement specimen in the detection unit 200. Examples of the computer program include a computer program for preparing a measurement specimen and a computer program for providing optical information on the measurement specimen, but are not particularly limited thereto. The storage unit 502 further stores reagent identification information to identify a reagent accommodated in the reagent accommodating portion 300, specimen preparation information on procedures in preparing a measurement specimen, and sample identification information to identify a blood sample accommodated in the sample accommodating portion 400. Examples of the reagent identification information include information on association of the type of reagent, the position of accommodating containers, and identifiers, but are not particularly limited thereto. Examples of the sample identification information include information on association of the type of blood sample, the position of accommodating containers, and identifiers, but are not particularly limited thereto. The CPU 501 executes the computer program for preparing a measurement specimen using the reagent identification information and specimen preparation information stored in the storage unit 502. Thus, the CPU 501 makes the specimen preparing section 100 of the measurement unit 20 prepare the measurement specimen.

[Configuration of Processing Apparatus]

As shown in FIG. 1, the processing apparatus 30 includes a calculator 31, a display unit 32, and an input unit 33. In the embodiment, the processing apparatus 30 is composed of a computer system. The calculator 31 includes a CPU 601 and a storage unit 602. The CPU 601 executes the computer program stored in the storage unit 602. Thus, the CPU 601 calculates clotting time. Examples of the display unit 32 include screen displays, but are not particularly limited thereto. The display unit 32 displays, for example, information on the calculated clotting time. Examples of the input unit 33 include keyboards and mice, but are not particularly limited thereto.

The storage unit 602 is installed with computer programs to be executed by the CPU 601, such as an operating system and an application program, as well as data used in executing the computer programs. Examples of the application program include computer programs for measuring the clotting time, but are not particularly limited thereto. The CPU 601 executes the computer program to measure clotting time stored in the storage unit 602. Thus, the CPU 601 makes the measurement device 10 measure clotting time.

[Modification of Measurement Device]

The sample transporting section 111, the first reagent transporting section 112, the second reagent transporting section 113, the third reagent transporting section 114, and the fourth reagent transporting section 115 may each be a flow path for flowing a sample or reagent. Examples of the flow paths include tubes, but are not particularly limited thereto.

The clotting time may be measured based on the increase in the viscosity due to blood clotting and other clotting information. When the clotting time is measured based on the increase in the viscosity due to blood clotting, the detection unit 200 includes a high frequency transmitting coil, a high frequency receiving coil, a cuvette mounting portion which is located between the high frequency transmitting coil and the high frequency receiving coil on which a cuvette accommodating a steel ball is mounted, and electromagnets provided at both ends of the cuvette mounting portion. The steel ball in the cuvette vibrates from side to side due to the magnetism generated by the electromagnets. The amplitude of vibration decreases as the viscosity increases. When the clotting of the measurement specimen starts, the viscosity of the measurement specimen increases, whereby the amplitude of the steel ball decreases. Therefore, the detection unit 200 detects changes in amplitude based on reception of a high-frequency wave transmitted by the high frequency transmitting coil by a high frequency receiving coil. The calculator 31 of the processing apparatus 30 calculates clotting time based on the detected changes in amplitude.

[Procedure of Measuring Clotting Time by Measurement Device]

Subsequently, an overview of a procedure of measuring the clotting time by the measurement device 10 will be described with reference to FIG. 2. In the following procedure, the controller 500 of the measurement unit 20 executes the computer program for preparing a measurement specimen which is stored in the storage unit 502 using the reagent identification information and specimen preparation information obtained from the storage unit 502. The controller 500 executes the computer program for providing optical information on the measurement specimen which is stored in the storage unit 502. The calculator 31 of the processing apparatus 30 executes the computer program for measuring the clotting time which is stored in the storage unit 602 using the obtained optical information.

In Step S1, the controller 500 of the measurement unit 20 makes the specimen preparing section 100 prepare a specimen. The specimen preparation in Step S1 is executed in accordance with the following procedures shown in FIGS. 3 and 4.

Thereafter, in Step S2, the controller 500 makes the specimen preparing section 100 add a calcium salt to the specimen. In Step S3, the controller 500 makes the detection unit 200 provide optical information on the measurement specimen. The addition of the calcium salt to the specimen in Step S2 and the provision of the optical information in Step S3 are executed in accordance with the procedure shown in FIG. 5.

Thereafter, in Step S4, the calculator 31 of the processing apparatus 30 executes a computer program for calculating clotting time to calculate the clotting time.

[Procedure of Preparing Specimen]

Figure 3:
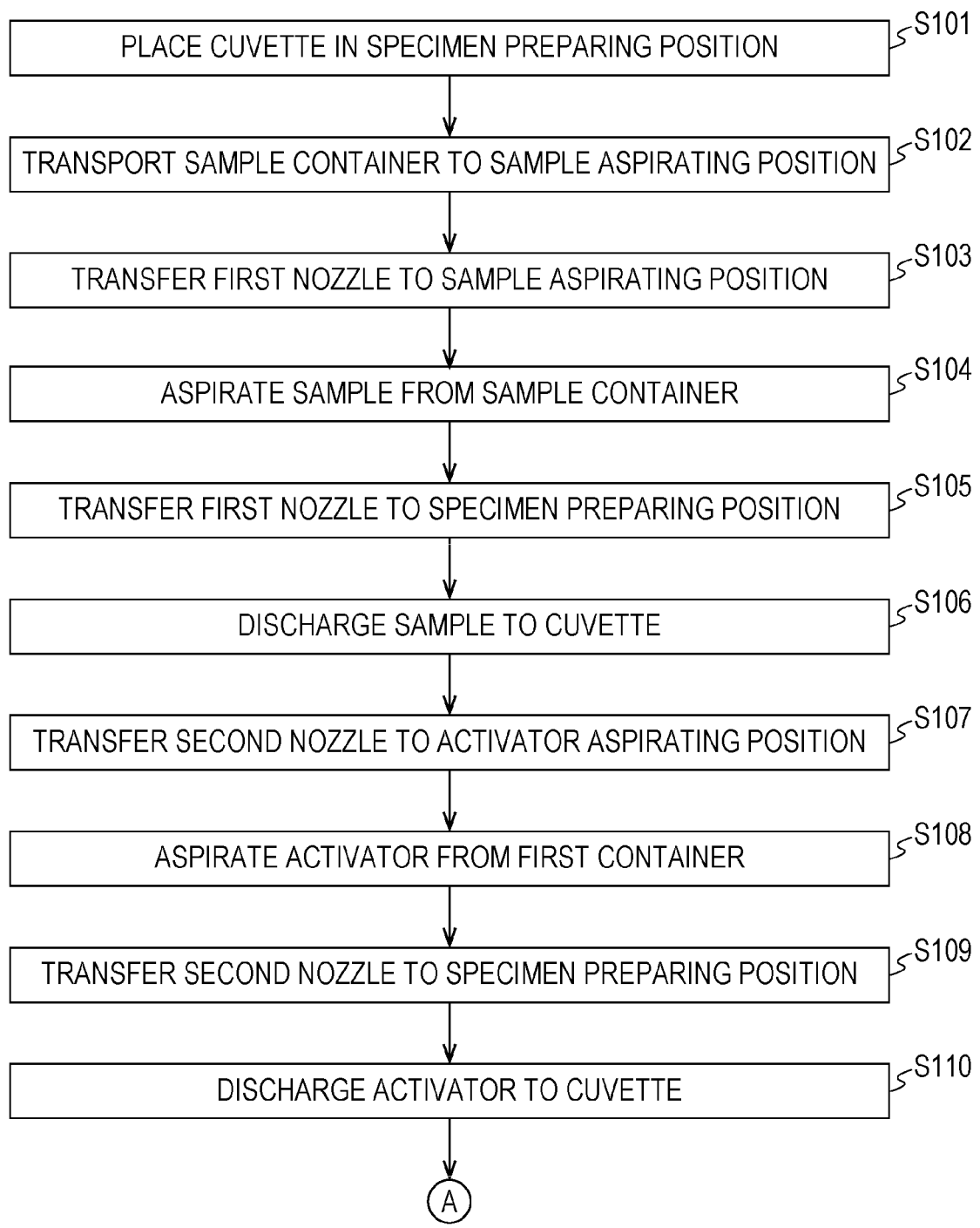
FIG. 3 is a flow chart showing a procedure of preparing a specimen.

Subsequently, an overview of a procedure of preparing a specimen by the measurement device 10 will be described with reference to FIGS. 3 and 4.

In Step S101, the controller 500 first makes the specimen preparing section 100 place the cuvette 90 in a specimen preparing position 62 in FIG. 1. Specifically, the controller 500 makes the specimen preparing section 100 mount the cuvette 90 in a first cuvette mounting portion 61 in FIG. 1. Thus, the cuvette 90 is placed in the specimen preparing position 62.

Then, in Step S102, the controller 500 makes the sample accommodating portion 400 transport the sample container 401 to the sample aspirating position 81 in FIG. 1. At this time, the controller 500 makes the sample accommodating portion 400 select a sample container 401 accommodating a desired blood sample based on the sample identification information stored in the storage unit 502. Then, the controller makes the sample accommodating portion 400 transport the selected sample container 401 so as to be located in the sample aspirating position 81.

Then, in Step S103, the controller 500 makes the specimen preparing section 100 transfer the first nozzle 101 to the sample aspirating position 81. Thereafter, in Step S104, the controller 500 makes the specimen preparing section 100 aspirate the blood sample from the sample container 401. Specifically, the controller 500 makes the specimen preparing section 100 aspirate the blood sample accommodated in the sample container 401 through the first nozzle 101.

Then, in Step S105, the controller 500 makes the specimen preparing section 100 transfer the first nozzle 101 to the specimen preparing position 62. Thereafter, in Step S106, the controller 500 makes the specimen preparing section 100 discharge the blood sample to the cuvette 90. Specifically, the controller 500 makes the specimen preparing section 100 discharge the blood sample aspirated by the first nozzle 101 to the cuvette 90.

Then, in Step S107, the controller 500 makes the specimen preparing section 100 transfer the second nozzle 102 to an activator aspirating position 71. Thereafter, in Step S108, the controller 500 makes the specimen preparing section 100 aspirate an activator from the first container 301. Specifically, the controller 500 makes the specimen preparing section 100 aspirate the activator accommodated in the first container 301 through the second nozzle 102.

Then, in Step S109, the controller 500 makes the specimen preparing section 100 transfer the second nozzle 102 to the specimen preparing position 62. Thereafter, in Step S110, the controller 500 makes the specimen preparing section 100 discharge the activator to the cuvette 90. Specifically, the controller 500 makes the specimen preparing section 100 discharge the activator aspirated through the second nozzle 102 to the cuvette 90.

Figure 4:
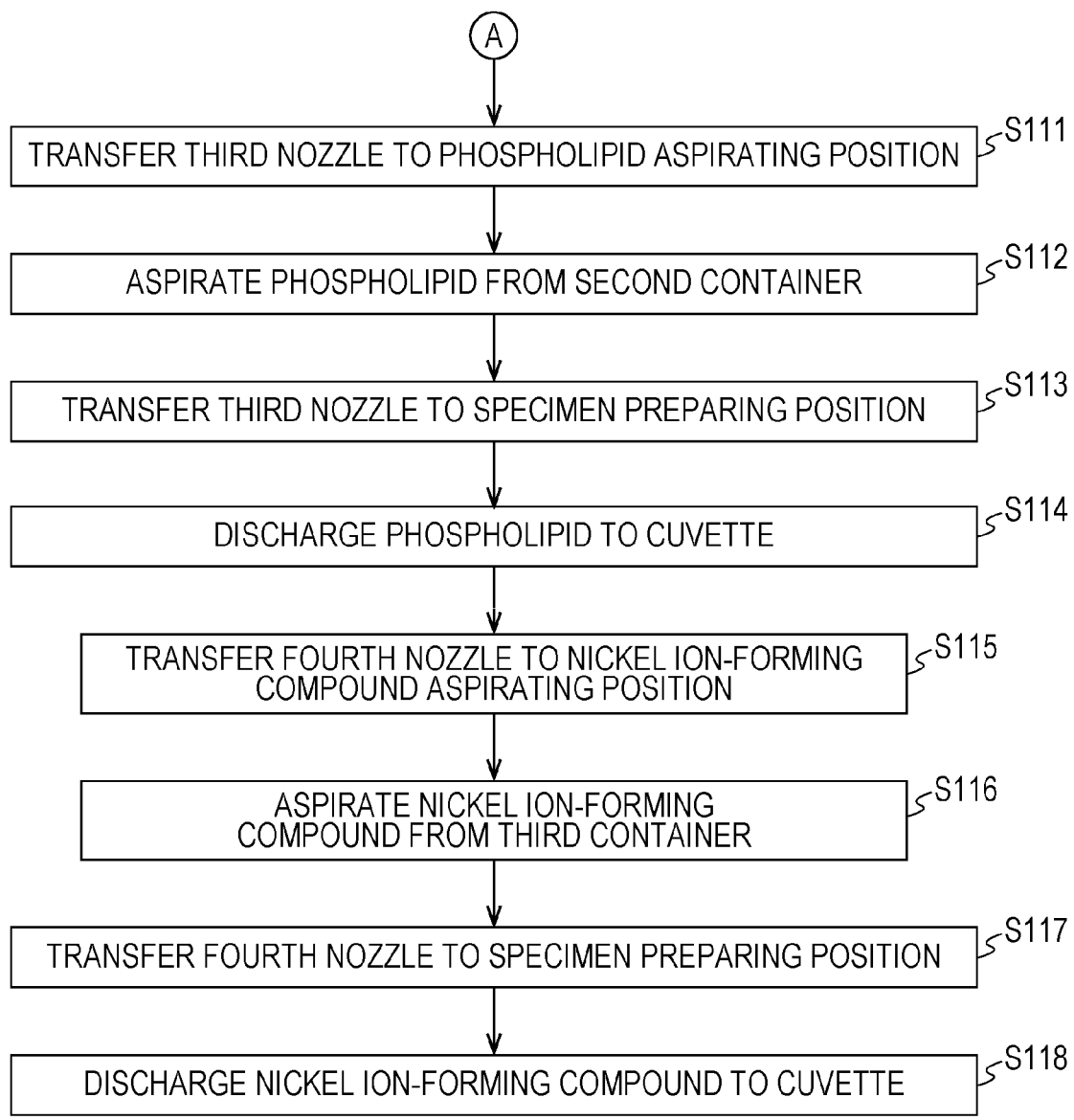
FIG. 4 is a flow chart showing a procedure of preparing a specimen.

Then, in Steps S111 to S114 of FIG. 4, the controller 500 makes the specimen preparing section 100 transfer the third nozzle 103 to the phospholipid aspirating position 72, aspirate a phospholipid from the second container 302, transfer the third nozzle 103 to the specimen preparing position 62, and discharge the phospholipid to the cuvette 90, respectively. Steps S111 to S114 are respectively the same as Steps S107 to S110 of FIG. 3 except for a series of operations including aspirating and discharging the phospholipid through the third nozzle 103.

Then, in Steps S115 to S118, the controller 500 makes the specimen preparing section 100 transfer the fourth nozzle 104 to a nickel ion-forming compound aspirating position 73, aspirate the nickel ion-forming compound from the third container 303, transfer the fourth nozzle 104 to the specimen preparing position 62, and discharge the nickel ion-forming compound to the cuvette 90, respectively. Steps S115 to S118 are respectively the same as Steps S107 to S110 of FIG. 3 except for a series of operations including aspirating and discharging the nickel ion-forming compound through the fourth nozzle 104. As a result, a specimen is obtained.

In the embodiment, the activator and phospholipid are added to the blood sample in this order. However, the activator and phospholipid may be simultaneously added thereto.

[Procedures of Adding Calcium Salt to Specimen and Obtaining Optical Information]

Subsequently, an overview of procedures of adding a calcium salt to a specimen by the measurement device 10 and obtaining optical information will be described with reference to FIG. 5.

Figure 5:
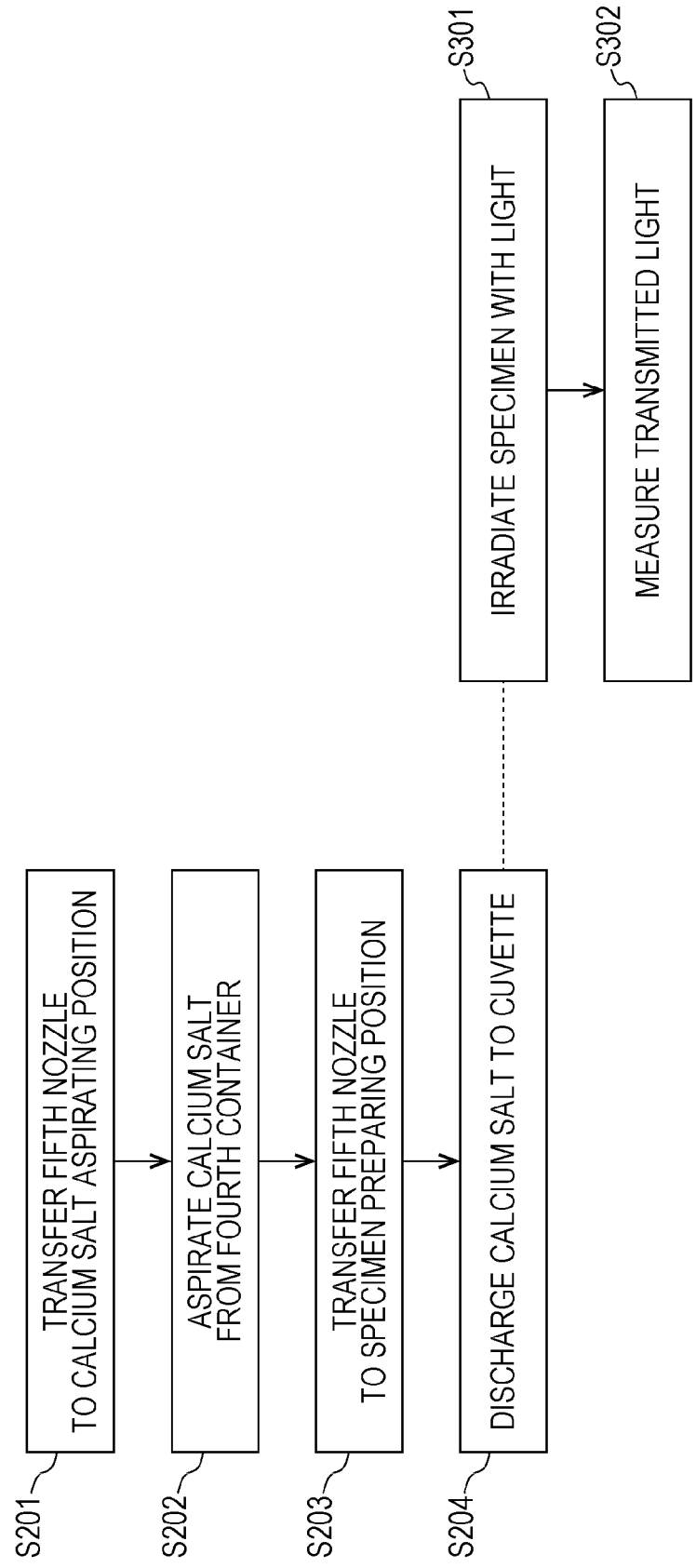
FIG. 5 is a flow chart showing procedures of steps of adding a calcium salt to a specimen and obtaining optical information.

In Steps S201 to S204 of FIG. 5, the controller 500 makes the specimen preparing section 100 transfer the fifth nozzle 105 to a calcium salt aspirating position 74, aspirate the calcium salt from the second container 302, transfer the fifth nozzle 105 to the specimen preparing position 62, and discharge the calcium salt to the cuvette 90, respectively. As a result, a measurement specimen is obtained. Steps S201 to S204 are respectively the same as Steps S107 to S110 of FIG. 3 except for a series of operations including aspirating and discharging the calcium salt through the fifth nozzle 105.

In Step S301, simultaneously with Step S204, the controller 500 makes the specimen preparing section 100 transfer the cuvette 90 to the second cuvette mounting portion 203 of the detection unit 200 through the cuvette transporting section 131. In Step S301, the controller 500 makes the detection unit 200 irradiate the measurement specimen with light. Specifically, the controller 500 makes the light irradiation unit 201 of the detection unit 200 emit light to the cuvette 90 mounted in the second cuvette mounting portion 203. As a result, the measurement specimen in the cuvette 90 is irradiated with light.

Then, in Step 302, the controller 500 makes the detection unit 200 measure the light from the measurement specimen. Specifically, the controller 500 makes the calculator 31 of the processing apparatus 30 output an electric signal corresponding to the amount of the transmitted light received by the light receiver 202 of the detection unit 200.

Figure 2:
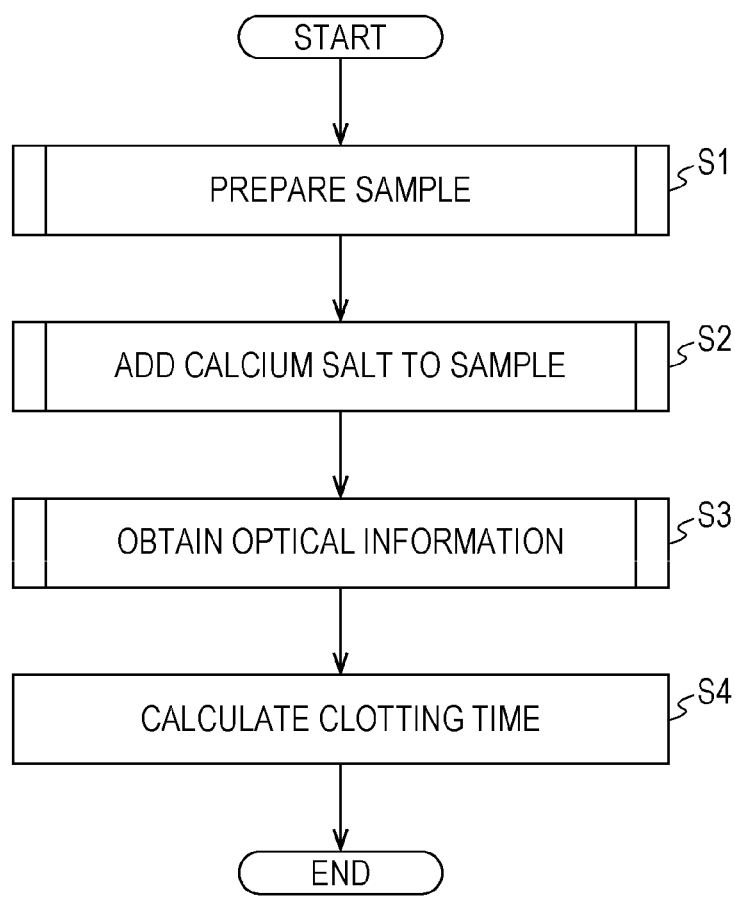
FIG. 2 is a flow chart showing a procedure of measuring the clotting time with a measurement device.

Thereafter, the process proceeds to the calculation of clotting time in Step S4 of FIG. 2.

[Modification of Operation Procedures]

A series of Steps S107 to S110 may be performed in conjunction with a series of Steps S111 to S114. A series of Steps S115 to S118 may be performed before both of the series of Steps S107 to S110 and the series of Steps S111 to S114.

When the clotting time is measured based on the increase in the viscosity due to blood clotting, one usable as the detection unit 200 is a detection unit that includes a high frequency transmitting coil, a high frequency receiving coil, a cuvette mounting portion on which a cuvette accommodating a steel ball is mounted, and an electromagnet. Here, the controller 500 makes the detection unit 200 detect changes in amplitude based on reception of a high-frequency wave transmitted by the high frequency transmitting coil of the detection unit 200 by the high frequency receiving coil. Then, the controller 500 makes the processing apparatus 30 output information on changes in amplitude detected by the detection unit 200. Thereafter, the calculator 31 of the processing apparatus 30 uses the obtained information on changes in amplitude, and executes the computer program for measuring the clotting time which is stored in the storage unit 602 to calculate the clotting time.

3. Clotting Time Measuring Reagent

The clotting time measuring reagent according to the embodiment is a clotting time measuring reagent used in the method for measuring a clotting time which contains a nickel ion-forming compound. The nickel ion-forming compound is the same as the nickel ion-forming compound in the measurement method.

The clotting time measuring reagent according to the embodiment may be a reagent that is substantially formed of a nickel ion-forming compound, or a reagent that contains a nickel ion-forming compound, an appropriate solvent, and further an adjuvant. The clotting time measuring reagent according to the embodiment does not substantially contain a phospholipid and an activator.

The clotting time measuring reagent may be provided in a solid state. In this case, examples of dosage forms of the clotting time measuring reagent include granules and dust formulations, but are not particularly limited thereto.

The clotting time measuring reagent may be in a state where the nickel ion-forming compound is dissolved in an appropriate solvent. In this case, examples of the solvent include desalinated and purified water and physiological saline, but are not particularly limited thereto.

When the clotting time measuring reagent is a reagent in a state where the nickel ion-forming compound is dissolved in an appropriate solvent, the content of the nickel ion-forming compound in the clotting time measuring reagent is preferably 1 µM or more, more preferably 0.1 mM or more, and preferably 50 mM or less, more preferably 10 mM or less.

When the clotting time measuring reagent further contains an adjuvant, examples of the adjuvant include a stabilizer and a preservative for the nickel ion-forming compound, but are not particularly limited thereto.

4. Reagent Kit

Figure 6:
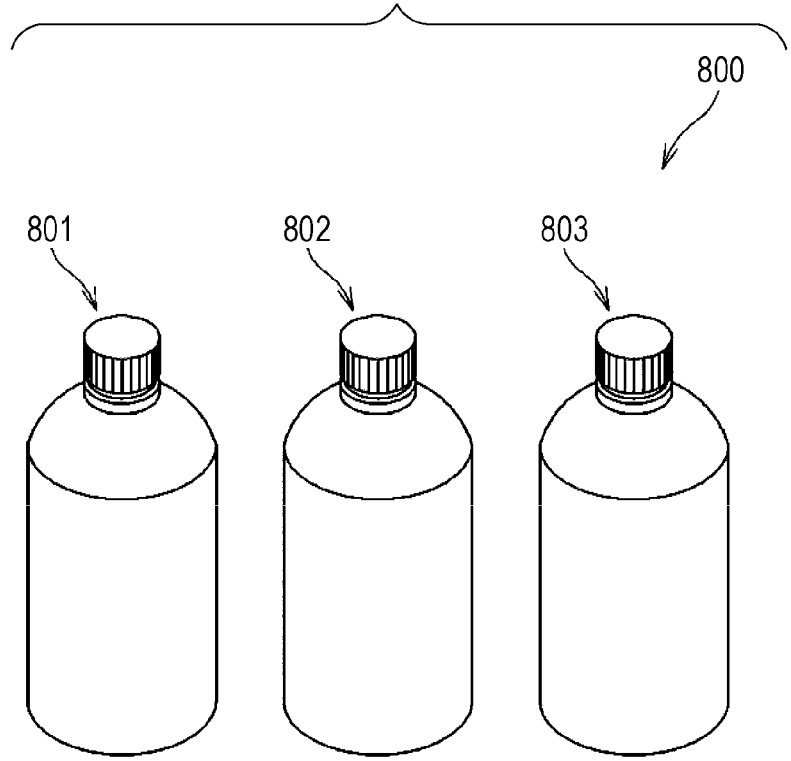
FIG. 6 is a configuration diagram of a reagent kit.

The reagent kit according to the embodiment is a reagent kit including a first reagent containing an activator and a phospholipid accommodated in a first reagent container, a second reagent containing a nickel ion-forming compound accommodated in a second reagent container, and a third reagent containing a calcium salt accommodated in a third reagent container. An example of the reagent kit according to the embodiment is a reagent kit 800 shown in FIG. 6, but is not particularly limited thereto. The reagent kit 800 shown in FIG. 6 includes a first reagent container 801, a second reagent container 802, and a third reagent container 803. The first reagent container 801 accommodates the first reagent containing an activator and a phospholipid. The second reagent container 802 accommodates the second reagent containing a nickel ion-forming compound. The third reagent container 803 accommodates the third reagent containing a calcium salt. The reagent kit may further include a package insert. The package insert may include the description of a procedure to perform the method for measuring a clotting time using the reagent kit according to the embodiment.

The concentration of the activator in the first reagent should be within a range in which the concentration in the measurement specimen can be adjusted in the range of the concentration in the measurement method. When the activator is an ellagic acid compound, usually, the concentration of the activator in the first reagent is preferably from 10 to 400 µM and more preferably from 50 to 150 µM. When the activator is silica, usually, the concentration of the activator in the first reagent is preferably from 0.1 to 1 mg/mL and more preferably from 0.2 to 0.6 mg/mL.

The concentration of the phospholipid in the first reagent should be within a range in which the concentration in the measurement specimen can be adjusted in the range of the concentration in the measurement method. Usually, the concentration of the phospholipid in the first reagent is preferably from 30 to 400 µg/mL and more preferably from 10 to 100 µg/mL. When the phospholipid is phosphatidylethanolamine, usually, the concentration of the phospholipid in the first reagent is preferably from 10 to 100 µg/mL and more preferably from 20 to 50 µg/mL. When the phospholipid is phosphatidylcholine, usually, the concentration of the phospholipid in the measurement specimen is preferably from 10 to 300 µg/mL and more preferably from 10 to 100 µg/mL. When the phospholipid is phosphatidylserine, usually, the concentration of the phospholipid in the measurement specimen is preferably from 1 to 75 µg/mL and more preferably from 2 to 15 µg/mL.

The second reagent may be a nickel ion-forming compound in a solid state, or may be in a state where a nickel ion-forming compound is dissolved in an appropriate solvent. The solvent is the same as the solvent in the clotting time measuring reagent.

When the second reagent is a reagent in a state where a nickel ion-forming compound is dissolved in an appropriate solvent, the concentration of the nickel ion-forming compound in the second reagent and the concentration of the phospholipid in the first reagent should be within a range in which the concentration in the measurement specimen can be adjusted in the range of the concentration in the measurement method. In this case, the concentration of the nickel ion-forming compound in the second reagent is preferably 1 µM or more, more preferably 0.1 mM or more, and preferably 50 mM or less, more preferably 10 mM or less.

The concentration of the calcium salt in the third reagent should be within a range in which the concentration in the measurement specimen can be adjusted in the range of the concentration in the measurement method. The concentration of the calcium salt in the third reagent is preferably from 2.5 to 40 mM and more preferably from 10 to 30 mM.

In the reagent kit according to the embodiment, the second reagent does not substantially contain the phospholipid and activator. In the reagent kit according to the embodiment, the first reagent does not substantially contain the nickel ion-forming compound.

The activator, phospholipid, nickel ion-forming compound, and calcium salt used in the reagent kit are the same as those used in the measurement method. Each of the reagent containers may accommodate an appropriate solvent, an adjuvant or the like, if appropriate. The solvent and adjuvant are the same as the solvent and reagent used in the clotting time measuring reagent. In the reagent kit according to the embodiment, the activator and phospholipid may be accommodated in separate containers.

EXAMPLES

The clotting time was measured with a fully automated clotting time measurement device (product name: CS-2000i, manufactured by Sysmex Corporation).

Example 1

In this example, normal plasma or test plasma was used as a blood sample. The used normal plasma is the normal plasma shown in Table 1. The used test plasma is the heparin-containing plasma shown in Table 1.

TABLE 1

| Blood sample | | | | | |
|---|---|---|---|---|---|
| Normal plasma | | | Pooled Normal Plasma (PBI) | LotA1156, manufactured by Precision BioLogic Incorporated | |
| Test plasma | Heparin-containing plasma | HE1 | Specimen containing 0.1 U/mL novo heparin | Addition of novo heparin to control plasma (product name: Coagtrol Lot. 022, manufactured by Sysmex Corporation) | Mixed with Pooled Normal Plasma (PBI) at 1:1 |
| | Heparin-containing plasma | HE2 | Specimen containing 0.1 U/mL novo heparin | Addition of novo heparin to control plasma (product name: Coagtrol Lot. 022, manufactured by Sysmex Corporation) | |
| | Heparin-containing plasma | HE3 | Specimen containing 0.2 U/mL novo heparin | Addition of novo heparin to control plasma (product name: Coagtrol Lot. 022, manufactured by Sysmex Corporation) | Mixed with Pooled Normal Plasma (PBI) at 1:1 |
| | Heparin-containing plasma | HE4 | Specimen containing 0.2 U/mL novo heparin | Addition of novo heparin to control plasma (product name: Coagtrol Lot. 022, manufactured by Sysmex Corporation) | |
| | Heparin-containing plasma | HE5 | Specimen containing 0.3 U/mL novo heparin | Addition of novo heparin to control plasma (product name: Coagtrol Lot. 022, manufactured by Sysmex Corporation) | Mixed with Pooled Normal Plasma (PBI) at 1:1 |
| | Heparin-containing plasma | HE6 | Specimen containing 0.3 U/mL novo heparin | Addition of novo heparin to control plasma (product name: Coagtrol Lot. 022, manufactured by Sysmex Corporation) | |
| | Heparin-containing plasma | HE7 | Sample containing 0.4 U/mL novo heparin | Addition of novo heparin to control plasma (product name: Coagtrol Lot. 022, manufactured by Sysmex Corporation) | Mixed with Pooled Normal Plasma (PBI) at 1:1 |
| | Heparin-containing plasma | HE8 | Specimen containing 0.4 U/mL novo heparin | Addition of novo heparin to control plasma (product name: Coagtrol Lot. 022, manufactured by Sysmex Corporation) | |
| | Heparin-containing plasma | HE9 | Specimen containing 0.6 U/mL novo heparin | Addition of novo heparin to control plasma (product name: Coagtrol Lot. 022, manufactured by Sysmex Corporation) | Mixed with Pooled Normal Plasma (PBI) at 1:1 |
| | Heparin-containing plasma | HE10 | Specimen containing 0.6 U/mL novo heparin | Addition of novo heparin to control plasma (product name: Coagtrol Lot. 022, manufactured by Sysmex Corporation) | |

Figure 7:
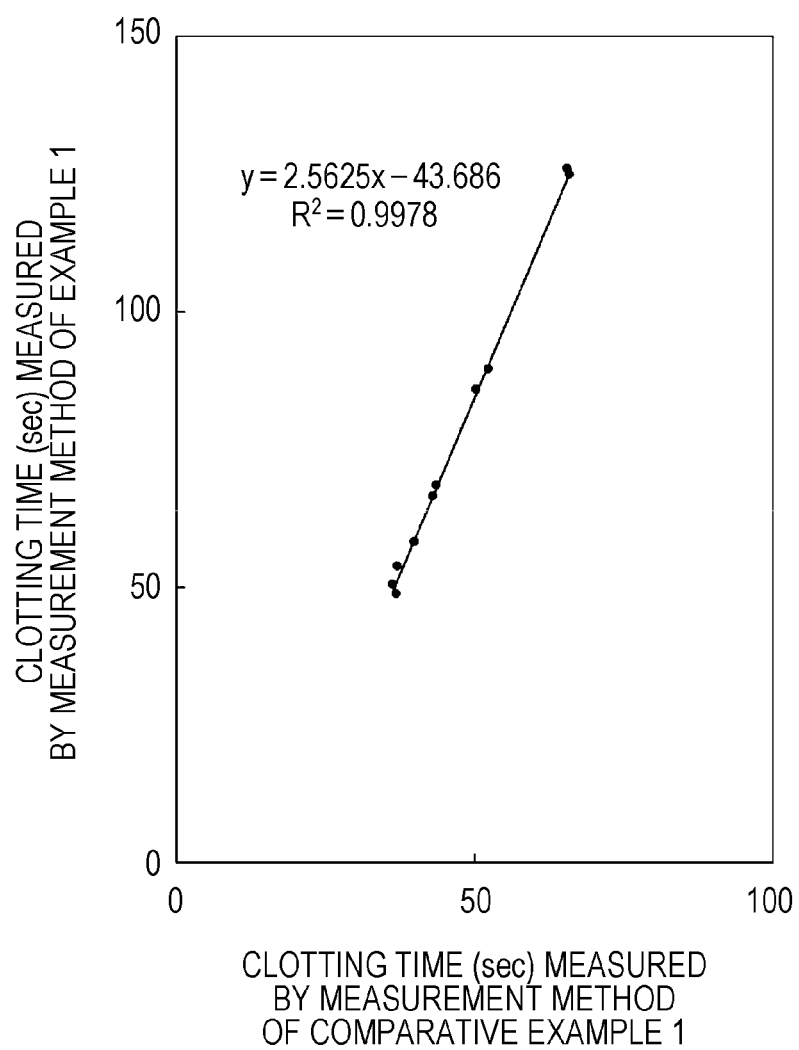
FIG. 7 is a graph showing results of comparison between the clotting time by the measurement method of Example 1 and the clotting time by the measurement method of Comparative Example 1.

First, 50 μL of a blood sample was heated at 37° C. for 60 seconds. Then, 50 μL of an APTT reagent (product name: PTT-LA (registered trademark), manufactured by Roche Diagnostics K.K.) was added to the heated blood sample and mixed therewith. The obtained mixture was heated at 37° C. for 20 seconds. Then, 20 μL of a 2.5 mM aqueous nickel acetate solution was added to the heated mixture and mixed therewith. The obtained mixture was heated at 37° C. for 170 seconds. As a clotting reaction accelerator, a 25 mM aqueous calcium chloride solution was added to the heated mixture and the clotting time was measured. Clotting times measured by the measurement method of Example 1 are shown in FIG. 7.

Comparative Example 1

In this comparative example, the used blood sample is the same blood sample as in Example 1. First, 50 μL of the blood sample was heated at 37° C. for 60 seconds. Then, 50 μL of an APTT reagent (product name: PTT-LA (registered trademark), manufactured by Roche Diagnostics K.K.) was added to the heated blood sample and mixed therewith. The obtained mixture was heated at 37° C. for 170 seconds. A 25 mM aqueous calcium chloride solution was added to the heated mixture and the clotting time was measured. Clotting times measured by the measurement method of Comparative Example 1 are shown in FIG. 7.

(Results)

The results in FIG. 7 show that the clotting time measured by the measurement method of Example 1 is longer than the clotting time measured by the measurement method of Comparative Example 1. Therefore, it is found that the measurement method of Example 1 allows the clotting time to be measured at high sensitivity, compared to the measurement method of Comparative Example 1, even if heparin-containing sample plasma is used.

Example 2 and Comparative Examples 2 to 5

Operations were performed in the same manner as in Example 1 except that the normal plasma shown in Table 1 as blood samples and HE2, HE4, HE6, HE8, and HE10 of the test plasma shown in Table 1 were used, and then the clotting times were measured (Example 2). The clotting time obtained by the measurement method of Example 2 was used, and the APTT ratio was calculated in accordance with Formula (I):

(APTT ratio)=(clotting time of test plasma/clotting time of normal plasma)      (I).

The operations was performed in the same manner as in Example 1 except that a 2.5 mM aqueous calcium chloride solution (Comparative Example 2), a 2.5 mM aqueous magnesium chloride solution (Comparative Example 3), a 2.5 mM aqueous copper sulfate solution (Comparative Example 4), and a 2.5 mM aqueous zinc chloride solution (Comparative Example 5) were used in place of a 2.5 mM aqueous nickel acetate solution, and the normal plasma shown in Table 1 as blood samples and HE2, HE4, HE6, HE8, and HE10 of the test plasma shown in Table 1 were used, and then the clotting time was measured. Calcium chloride, magnesium chloride, copper sulfate, and zinc chloride are compounds that form divalent ions (divalent cations) other than divalent nickel ions.

Figure 8:
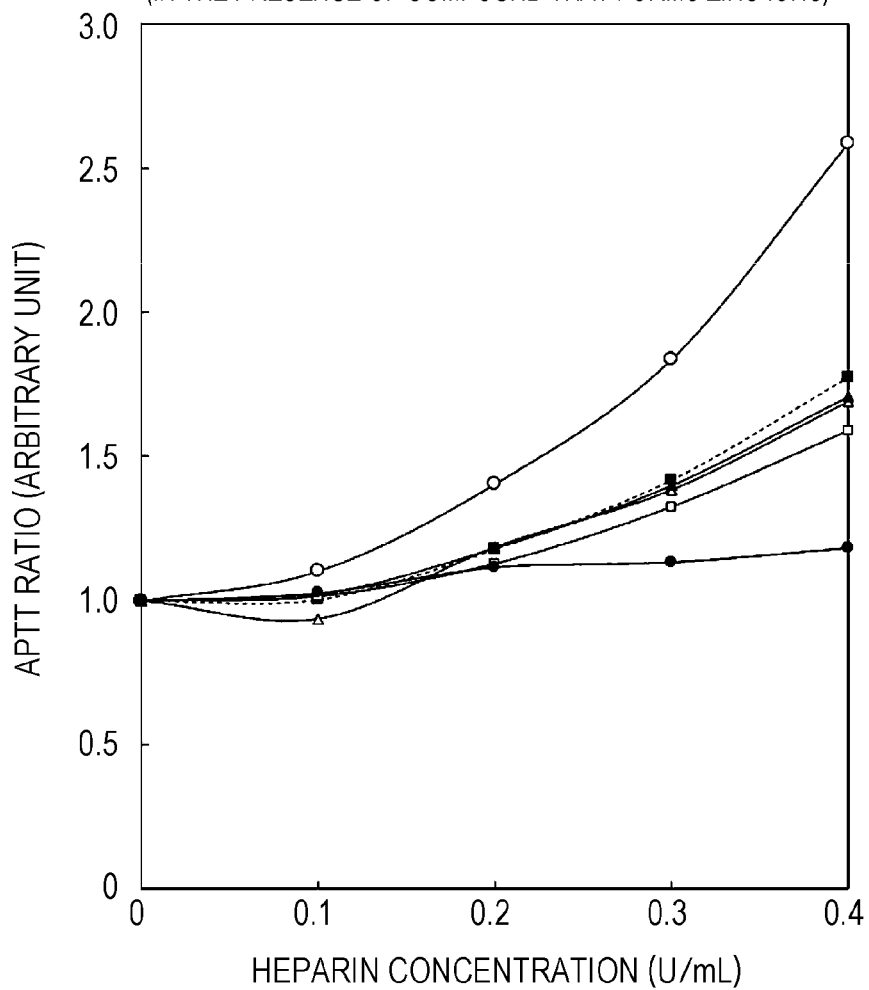
FIG. 8 is a graph showing results of an examined relationship between heparin concentration and APTT ratio in Example 2 and Comparative Examples 2 to 5.

The clotting times obtained by the measurement methods of Comparative Examples 1 to 5 were used and the APTT ratios were measured in accordance with Formula (I). FIG. 8 shows the results of the examined relationship between heparin concentration and APTT ratio. In the graph, a white circle represents the APTT ratio measured by the measurement method of Example 2 (in the presence of the nickel ion-forming compound), a black square represents the APTT ratio measured by the measurement method of Comparative Example 1 (in the absence of the compound that forms divalent cations), a white triangle represents the APTT ratio measured by the measurement method of Comparative Example 2 (in the presence of the compound that forms calcium ions), a black triangle represents the APTT ratio measured by the measurement method of Comparative Example 3 (in the presence of the compound that forms magnesium ions), a white square represents the APTT ratio measured by the measurement method of Comparative Example 4 (in the presence of the compound that forms copper ions), and a black dot represents the APTT ratio measured by the measurement method of Comparative Example 5 (in the presence of the compound that forms zinc ions).

The results shown in FIG. 8 show that the APTT ratio measured by the measurement method of Example 2 is larger than the APTT ratios measured by the measurement methods of Comparative Examples 1 to 5. Therefore, as in Example 2, it is found that when the nickel ion-forming compound is used, the sensitivity to the heparin-containing sample is improved, compared to the case of using other compounds that forms divalent ions (Comparative Examples 2 to 5) and the case of the conventional method (Comparative Example 1). On the other hand, as in the case of the measurement methods of Comparative Examples 2 to 5, it is found that when other compounds that form divalent ions are used, the APTT ratio is equal to or lower than the APTT ratio measured by the measurement method of Comparative Example 1.

These results show that, in the clotting time measurement using the APTT reagent, the clotting time can be measured at high sensitivity by adding a compound that forms nickel ions among divalent cations to a blood sample before adding a clotting reaction accelerator.

What is claimed is:

1. A method for measuring an activated partial thromboplastin time, comprising the steps of:
   (A) mixing a blood sample, an activator, a phospholipid, and a nickel ion-forming compound to obtain a specimen comprising a free nickel ion; and
   (B) mixing the specimen obtained in step (A) with a calcium salt to prepare a measurement specimen and measuring the activated partial thromboplastin time of the measurement specimen in the presence of the free nickel ion,
   wherein step (A) includes the steps of:
   (A1-1) mixing the blood sample, the activator, and the phospholipid to obtain a mixture and incubating the mixture of the blood sample, activator and the phospholipid for 10 to 150 seconds; and
   (A1-2) mixing the mixture obtained in step (A1-1) with the nickel ion-forming compound.

2. The method according to claim 1, wherein the nickel ion-forming compound in the mixture obtained in step (A) has a final concentration of 0.1 μM or more and less than 10 mM.

3. The method according to claim 1, wherein the nickel ion-forming compound in the mixture obtained in step (A) has a final concentration of 0.1 mM or more and less than 5 mM.

4. The method according to claim 1, wherein, in step (B), the mixture obtained in step (A) is incubated in a predetermined condition, and then a calcium salt is added to the mixture.

5. The method according to claim 4, wherein the predetermined condition is a condition of incubation at a temperature of 30° C. or more and 45° C. or less.

6. The method according to claim 4, wherein the predetermined condition is a condition of incubation at a temperature of 36° C. or more and 38° C. or less.

7. The method according to claim 4, wherein the predetermined condition is a condition of incubation for 1 minute or more and 6 minutes or less.

8. The method according to claim 4, wherein the predetermined condition is a condition of incubation for 2 minutes or more and 5 minutes or less.

9. The method according to claim 4, wherein the predetermined condition is a condition of incubation at a temperature of 30° C. or more and 45° C. or less for 1 minute or more and 6 minutes or less.

10. The method according to claim 1, wherein the nickel ion-forming compound is a compound selected from the group consisting of nickel acetate, nickel phosphide, nickel sulfide, nickel chloride, nickel sulfate, and nickel benzoate.

11. The method according to claim 1, wherein the activator comprises an ellagic compound, silica, kaolin, diatomaceous earth or any mixture thereof.

12. The method according to claim 1, wherein in the step of (A1-1), the mixture of the blood sample, activator and the phospholipid is incubated for 30 to 90 seconds.

\* \* \* \* \*